United States Patent [19]

Maurer et al.

[11] 4,013,794
[45] Mar. 22, 1977

[54] O-ALKYL-S-ALKYL-O-PHENYL PHOSPHATES AND INSECTICIDAL AND ACARICIDAL METHOD OF USE

[75] Inventors: Fritz Maurer; Hans-Jochem Riebel; Lothar Rohe, all of Wuppertal; Ingeborg Hammann, Cologne; Wilhelm Stendel, Wuppertal, all of Germany

[73] Assignee: Bayer Aktiengesellschaft, Leverkusen, Germany

[22] Filed: Jan. 13, 1976

[21] Appl. No.: 648,849

Related U.S. Application Data

[63] Continuation-in-part of Ser. No. 518,838, Oct. 29, 1974, abandoned.

[30] Foreign Application Priority Data

Nov. 17, 1973 Germany .......................... 2357526

[52] U.S. Cl. .............................. 424/212; 260/949; 424/216
[51] Int. Cl.² ....................... A01N 9/36; C07F 9/18
[58] Field of Search ........... 260/949, 941; 424/212, 424/216

[56] References Cited

UNITED STATES PATENTS 2,803,580  8/1957  Metivier ....................... 260/949 X
3,322,864  5/1967  Schrader ....................... 260/949 X
3,825,636  7/1974  Kishino et al. ................ 260/949 X

FOREIGN PATENTS OR APPLICATIONS 255,279  2/1963  Australia .......................... 260/964

Primary Examiner—Richard L. Raymond
Attorney, Agent, or Firm—Burgess, Dinklage & Sprung

[57] ABSTRACT

O-Alkyl-S-alkyl-O-phenyl phosphates of the formula

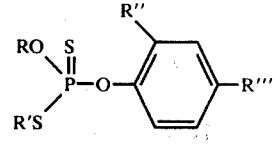

in which
R and R' each is lower alkyl,
R'' is hydrogen or halogen, and
R''' is a lower alkylsulfonyl, halogeno-lower alkylsulfonyl or 1-fluoro-1-carbo-lower alkoxy-methylmercapto,
which possess insecticidal and acaricidal properties.

11 Claims, No Drawings

O-ALKYL-S-ALKYL-O-PHENYL PHOSPHATES AND INSECTICIDAL AND ACARICIDAL METHOD OF USE

This application is a continuation-in-part of application Ser. No. 518,838, filed Oct. 29, 1974, now abandoned.

The present invention relates to and has for its objects the provision of particular new O-alkyl-S-alkyl-O-phenyl phosphate, i.e. O-alkyl-S-alkyl-O-(alkylsulfonylphenyl)-, (haloalkylsulfonylphenyl)- or (1-fluoro-1-carbalkoxy-methylmercapto-phenyl)-phosphates, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,803,580 that O-phenylthionophosphoric acid esters, such as O,O-diethyl-O-(4-chloromethylsulfonylphenyl)-thionophosphoric acid ester (Compound A), have insecticidal and acaricidal properties. However, these compounds have a high toxicity towards warm-blooded animals.

The present invention provides, as new compounds, the O-phenylthionothiolphosphoric acid esters of the general formula

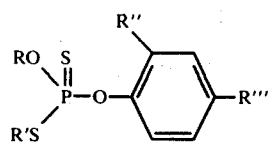

in which
R and R' each is lower alkyl,
R" is hydrogen or halogen, and
R''' is lower alkylsulfonyl, halogeno-lower alkylsulfonyl or 1-fluoro-1-carbo-lower alkoxy-methylmercapto.

Preferably, R and R' are each straight-chain or branched alkyl with 1 to 4 carbon atoms, R" is hydrogen, chlorine or bromine, and R''' is straight-chain or branched alkysulfonyl radical with 1 to 4, especially 1 to 3, carbon atoms, a halogeno-lower alkylsulfonyl radical with 1 to 4 carbon atoms such as chloromethylsulfonyl and 2-chloroethylsulfonyl, or a 1-fluoro-1-carbalkoxymethylmercapto radical with 1 to 4, especially 1 to 3, carbon atoms in the alkyl group. Those compounds wherein R is ethyl and R' is n-propyl are especially preferred.

Surprisingly, the O-phenylthionothiolphosphoric acid esters according to this invention are distinguished by a substantially higher insecticidal and acaricidal action, coupled with a very low toxicity to warm-blooded animals, than the prior-art compounds of analogous structure and of the same type of action. The compounds according to the invention thus represent a genuine enrichment of the art.

The present invention also provides a process for the preparation of an O-phenylthionothiolphosphoric acid ester of the formula (I), in which a substituted phenol of the general formula

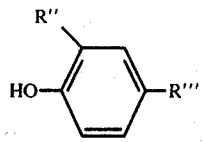

in which
R" and R''' have the above-mentioned meanings, is reacted, in the presence of an acid-binding agent or in the form of an alkali metal salt, alkaline earth metal salt or ammonium salt thereof, with an O,S-dialkylthionothiolphosphoric acid diester halide of the general formula

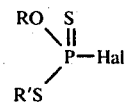

in which
R and R' have the above-mentioned meanings, and Hal is halogen, preferably chlorine.

If 2-bromo-4-chloromethylsulfonylphenol and O-ethyl-S-sec.-butyl-thionothiolphosphoric acid diester chloride are used as starting materials, the course of the reaction can be represented by the following equation:

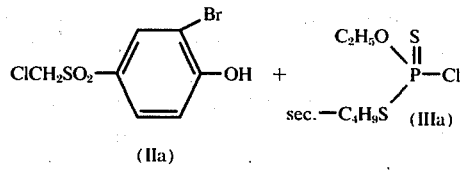

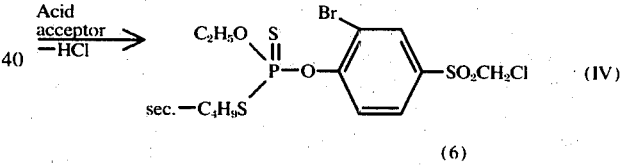

(6)

Phenol derivatives (II) which can be used in the preparative process are described in the literature and can be prepared in accordance with known processes, as can the O,S-dialkylthionothiolphosphoric acid diester halides (III), e.g. USSR Patent Specification No. 184,863 and published Japanese Patent Application No. 5,536/72.

The following may be mentioned as examples of the phenol derivatives (II): 4-methylsulfonyl-, 4-ethylsulfonyl-, 4-n-propylsulfonyl-, 4-isopropylsulfonyl-, 4-chloromethylsulfonyl-, 4-(2'-chloroethylsulfonyl)-, 4-(1'-fluoro-1'-carbomethoxymethylmercapto)-, 4-(1'-fluoro-1'-carbethoxymethylmercapto)-, 4-(1'-fluoro-1'-carbo-n-propoxymethylmercapto)- or 4-(1'-fluoro-1'-carbo-isopropoxymethylmercapto)-phenol and the corresponding 2-chloro and 2-bromo derivatives.

The following may be mentioned as examples of the O,S-dialkylthionothiolphosphoric acid diester halides (III): O,S-dimethyl-, O,S-diethyl-, O,S-di-n-propyl-, O,S-di-isopropyl-, O,S-di-n-butyl-, O,S-di-sec.-butyl-, O,S-di-tert.-butyl-, O-ethyl-S-n-propyl, O-ethyl-S-isopropyl-, O-ethyl-S-n-butyl-, O-ethyl-S-sec.-butyl-, O-ethyl-S-isobutyl-, O-ethyl-S-tert.-butyl-, O-n-propyl-S- methyl-, O-n-propyl-S-ethyl-, O-n-propyl-S-isopropyl-, O-n-propyl-S-n-butyl-, O-n-propyl-S-sec.-butyl-, O-n-propyl-S-tert.-butyl-, O-n-butyl-S-ethyl or O-n-butyl-S-n-propyl-thionothiolphosphoric acid diester chloride.

The preparative process is preferably carried out with the use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-acceptors can be used as acid-binding agents. Alkali metal carbonates and alkali metal alcoholates, such as sodium carbonate, potassium carbonate, sodium methylate, potassium methylate, sodium ethylate and potassium ethylate, have proved particularly suitable, as have aliphatic, aromatic or heterocyclic amines, for example triethylamine, trimethylamine, dimethylaniline, dimethylbenzylamine and pyridine.

Instead of carrying out the reaction in the presence of an acid-acceptor, it is equally possible first to prepare a salt, preferably an alkali metal salt or ammonium salt, of the phenol derivative (II), and then to react the salt further.

The reaction temperature can be varied within a fairly wide range. In general, the reaction is carried out at between 10° and 100° C, and preferably at from 20° to 70° C.

The reaction is in general allowed to take place under normal pressure.

To carry out the process, preferably equimolar amounts of the starting materials are employed; an excess of one or other reactant produces no significant advantages. The reaction is optionally carried out in a solvent and preferably in the presence of an acid acceptor, at the temperatures indicated. After stirring the mixture for one or more hours at an elevated temperature, the salt-like precipitate is filtered off. The filtrate is poured into an organic solvent, for example toluene, and worked up in the usual manner, for example by washing, drying and distillation of the organic phase.

The new compounds are obtained in the form of oils which in most cases cannot be distilled without decomposition but can be freed of the last volatile constituents by so-called "slight distillation", that is to say be prolonged heating under reduced pressure to moderately elevated temperatures, and can be purified in this way. They are characterized by their refractive indexes.

As already mentioned, the O-phenylthionothidphosphoric acid esters according to this invention are distinguished by an outstanding insecticidal, including soil-insecticidal, and acaricidal activity. The compounds are active against plant pests, pests harmful to health and pests of stored products and, in the field of veterinary medicine, against animal parasites (ectoparasites) such as parasitic fly larvae. The compounds according to the invention can be employed successfully as pesticides in plant protection and in the hygiene field for protection of stored products and the veterinary field because they couple a low toxicity towards warm-blooded animals with a good action against both sucking and biting insects.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly ((*Drosophila melanogaster*), the Mediterranean fruit fly (*Ceratitus capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, the example the broad mite (*Hemitarsonemus latus*) and the cyclamen mite (*Tarsonemus pallidus*); finally, ticks, such as the replapsing fever tick (*Ornithodorus moubata*).

When applied against pests harmful to health and pests of stored products, particularly flies and mosquitoes, the products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolines, clays, alumina, silica, chalk, i.e. calcium carbonate, talc, attapulgite, montomorillonite, kieselguhr, etc.) and ground synthetic minerals (e.g. highly dispersed silicic acid, silicates, e.g. alkali silicates, etc.); whereas the folloawing may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%., preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier assistant, e.g. a surface-active agent, such as an emulsifying agent and/or a dispersing agent, and an amount of the active compound which is effective for the purpose in question and which is generally between about 0.0001–95%., and preferably 0.01–95%., by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarid, which comprises applying to at least one of correspondingly (a) such insects, (b) such acarids, and (c) the corresponding habitate thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*), which has a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compounds was determined by counting the dead mites. The degree of destruction thus obtained is expressed as a percentage: 100% means that all the spider mites were killed, whereas 0% means that none of the spider mites were killed.

The active compounds, the concentrations of the active compounds, the evaluation times and the results can be seen from the following table:

Table 1

| Active compound | Active compound concentration in % | Degree of destruction in % after 2 days |
|---|---|---|
| (A) (known) Cl—CH$_2$—SO$_2$—C$_6$H$_4$—O—P(S)(OC$_2$H$_5$)$_2$ | 0.1<br>0.01 | 50<br>0 |
| (3) Cl—CH$_2$—SO$_2$—C$_6$H$_3$(Cl)—O—P(S)(OC$_2$H$_5$)(SC$_3$H$_7$-n) | 0.1<br>0.01 | 100<br>60 |

EXAMPLE 2

Toxicity test (peroral)

Test animal: Albino rat (*Rattus norvegicus*)
Evaluation after: 7 days

To produce a suitable preparation of active compound, 3 parts by weight of active compound were mixed with 2.8 parts by weight of highly dispersible silica and 4.2 parts by weight of talc. Suspensions which contained, in 1 ml of liquid, the amount of active compound to be applied per 100 g of animal weight, were prepared from the above active-compound concentrate, with a little added powdered vegetable gum, by grinding with water. Dosing was effected volumetrically after weighing the test animals. A steel, knob-ended probe was used for oral administration. The evaluation was carried out in each case after the end of the above-mentioned time interval, calculated from the administration of the active compound.

The LD$_{50}$ values (dose of active compound at which 50% of the treated animals were killed) were determined in the usual manner from the mortality figures of the doses, which were varied in geometrical progression.

The active compounds and LD$_{50}$ values can be seen from the table which follows Table B

| (Toxicity test/albino rat/peroral) | |
|---|---|
| Active compound | LD$_{50}$ values (in mg/kg of body weight) |
| (A) (known) Cl—CH$_2$—SO$_2$—C$_6$H$_4$—O—P(S)(OC$_2$H$_5$)$_2$ | 2.5 – 5 |
| (5) CH$_3$—SO$_2$—C$_6$H$_3$(Cl)—O—P(S)(OC$_2$H$_5$)(SC$_3$H$_7$-n) | 50 – 100 |
| (1) CH$_3$—SO$_2$—C$_6$H$_3$(Br)—O—P(S)(OC$_2$H$_5$)(SC$_3$H$_7$-n) | 50 – 100 |
| (2) Cl—CH$_2$SO$_2$—C$_6$H$_4$—O—P(S)(OC$_2$H$_5$)(SC$_3$H$_7$-n) | approx. 250 |
| | 100 – 250 |
| (3) Cl—CH$_2$—SO$_2$—C$_6$H$_3$(Cl)—O—P(S)(OC$_2$H$_5$)(SC$_3$H$_7$-n) | |
| (4) C$_2$H$_5$O—CO—CHF—C$_6$H$_4$—O—P(S)(OC$_2$H$_5$)(SC$_3$H$_7$-n) | 100 – 250 |

EXAMPLE 3

Test with parasitic fly larvae

Solvent: 35 parts by weight of ethylene polyglycol monomethyl ether

Emulsifier: 35 parts by weight of nonylphenol polyglycol ether.

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 ml of horse muscle. 0.5 ml of the preparation of active compound was applied to this horse meat. After 24 hours, the degree of destruction was determined in %. 100% means that all the larvae had been killed and 0% means that no larvae had been killed.

The test results obtained can be seen from the table which follows:

EXAMPLE 4

Plutella Test

Solvent: 3 parts by weight Acetone

Emulsifier: 1 part by weight Alkylaryl polyglycol ether

To produce a suitable preparation of active compound, 1 part by weight of the active compound is mixed with the stated amount of solvent and the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation times and the results can be seen from the following Table 4:

Table 3

Test with parasitic fly larvae (*Lucilia cuprina* res.)

| Active compound | Active compound concentration in ppm | Degree of destruction in % |
|---|---|---|
| 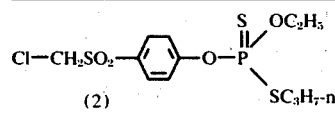 (2) | 100<br>30<br>10<br>1 | 100<br>100<br>100<br>0 |
| 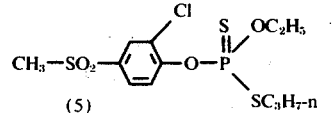 (5) | 100<br>30<br>10<br>3<br>1 | 100<br>100<br>100<br>100<br>0 |
| 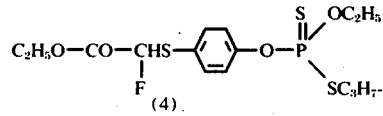 (4) | 100<br>30<br>10 | 100<br>>50<br>0 |

Table 4

(Plutella Test)

| Active compound (constitution) | Concentration of active compound in % | Degree of destruction in % after 3 days |
|---|---|---|
| 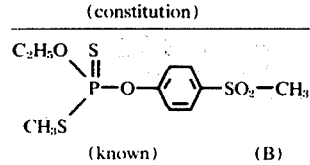<br>(known) (B) | 0.1<br>0.02<br>0.004 | 100<br>85<br>0 |
| 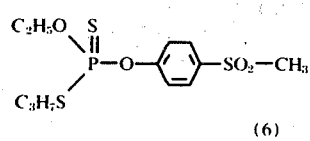<br>(6) | 0.1<br>0.02<br>0.004 | 100<br>100<br>100 |
| 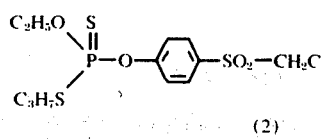<br>(2) | 0.1<br>0.02<br>0.004 | 100<br>100<br>100 |

Table 4-continued

| (Plutella Test) Active compound (constitution) | Concentration of active compound in % | Degree of destruction in % after 3 days |
|---|---|---|
| $\text{C}_2\text{H}_5\text{O}\diagdown\underset{\text{C}_3\text{H}_7\text{S}\diagup}{\overset{\text{S}}{\underset{\|}{\text{P}}}}-\text{O}-\text{(2-Cl,4-SO}_2\text{CH}_3\text{-C}_6\text{H}_3)$ (5) | 0.1<br>0.02<br>0.004<br>0.0008 | 100<br>100<br>100<br>100 |
| $\text{C}_2\text{H}_5\text{O}\diagdown\underset{n\text{C}_3\text{H}_7\text{S}\diagup}{\overset{\text{S}}{\underset{\|}{\text{P}}}}-\text{O}-\text{(2-Cl,4-Cl-C}_6\text{H}_3)$ (known) (C) | 0.1<br>0.02<br>0.004<br>0.0008 | 100<br>100<br>100<br>0 |
| $\text{C}_2\text{H}_5\text{O}\diagdown\underset{n\text{C}_3\text{H}_7\text{S}\diagup}{\overset{\text{S}}{\underset{\|}{\text{P}}}}-\text{O}-\text{(2-Br,4-SO}_2\text{CH}_3\text{-C}_6\text{H}_3)$ (1) | 0.1<br>0.02<br>0.004<br>0.0008 | 100<br>100<br>100<br>90 |

EXAMPLE 5

Phaedon-Larvae-Test

Solvent: 3 parts by weight Acetone
Emulsifier: 1 part by weight Alkylaryl polyglycol ether To produce a suitable preparation of the particular active compound, 1 part by weight of such active compound is mixed with the stated amount of solvent and the stated amount of emulsifier, and the resulting concentrate is diluted with water to the desired final concentration.

Cabbage leaves (*Brassica oleracea*) are sprayed with the preparation of the given active compound until dripping wet and then infested with the larvae of mustard beetles (*Phaedon cochleariae*).

After specified periods of time, the degree of destruction is determined as a percentage: 100% means that all the beetle larvae are killed, 0% means that none of the beetle larvae are killed. The active compounds, the concentrations used, the evaluation time and the results obtained can be seen from the following Table 5:

Table 5

| (Phaedon-Larvae-Test) Active compound (constitution) | Concentration of active compound in % | Degree of destruction in % after 3 days |
|---|---|---|
| $\text{C}_2\text{H}_5\text{O}\diagdown\underset{\text{C}_3\text{H}_7\text{S}\diagup}{\overset{\text{S}}{\underset{\|}{\text{P}}}}-\text{O}-\text{(2-Cl,4-Cl-C}_6\text{H}_3)$ (known) (C) | 0.1<br>0.02<br>0.004 | 100<br>100<br>20 |
| $\text{C}_2\text{H}_5\text{O}\diagdown\underset{\text{CH}_3\text{S}\diagup}{\overset{\text{S}}{\underset{\|}{\text{P}}}}-\text{O}-\text{(4-SO}_2\text{CH}_3\text{-C}_6\text{H}_4)$ (known) (B) | 0.1<br>0.02<br>0.004 | 100<br>100<br>15 |
| $\text{C}_2\text{H}_5\text{O}\diagdown\underset{\text{C}_3\text{H}_7\text{S}\diagup}{\overset{\text{S}}{\underset{\|}{\text{P}}}}-\text{O}-\text{(4-SO}_2\text{CH}_3\text{-C}_6\text{H}_4)$ (6) | 0.1<br>0.02<br>0.004 | 100<br>100<br>100 |
| $\text{C}_2\text{H}_5\text{O}\diagdown\underset{n\text{C}_3\text{H}_7\text{S}\diagup}{\overset{\text{S}}{\underset{\|}{\text{P}}}}-\text{O}-\text{(2-Br,4-SO}_2\text{CH}_3\text{-C}_6\text{H}_3)$ (1) | 0.1<br>0.02<br>0.004 | 100<br>100<br>100 |

EXAMPLE 6

Myzus Test (contact action)

Solvent: 3 parts by weight Acetone
Emulsifier: 1 part by weight Alkylaryl polyglycol ether To produce a suitable preparation of active compound, 1 part by weight of the active compound is mixed with the stated amount of solvent and the stated amount of emulsifier and the concentrate is diluted with water to the desired concentration.

Cabbage plants (*Brassica oleracea*) which have been heavily infested with peach aphids (*Myzus persicae*) are sprayed with the preparation of the active compound until dripping wet.

After the specified periods to time, the degree of destruction is determined as a percentage: 100% means that all the aphids are killed whereas 0% means that none of the aphids are killed.

The active compounds, the concentrations of the active compounds, the evaluation times and the results can be seen from the following Table 6:

stirred for a further hour at 40° to 45° C and a vigorous stream of air was then blown through the reaction solution for 10 minutes. After adding 0.5 g of sodium molybdate, 145 g of 50% strength hydrogen peroxide were added dropwise at 50° C. When the reaction had subsided, the batch was stirred for a further hour at 60° to 65° C; the excess peroxide was then destroyed with about 7 ml of 40% strength sodium bisulfite solution. Thereafter, a solution of 160 g (4 moles) of sodium hydroxide in 400 ml of water was added to the reaction mixture, which was kept below 50° C. The reaction of the mixture was then allowed to finish without cooling. The mixture was stirred for a further hour at 55° to 60° C and then cooled to 0° C, and the sodium phenolate which had precipitated was filtered off. It was dissolved in about 500 ml of water and aqueous hydrochloric Table 6

| Active compound (constitution) | (Myzus Test) Concentration of active compound in % | Degree of destruction in % after 1 day |
| --- | --- | --- |
| 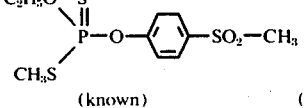 (known) (B) | 0.1 0.02 | 35 0 |
| 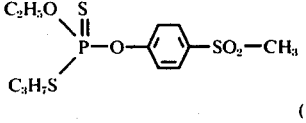 (6) | 0.1 0.02 | 100 60 |
| 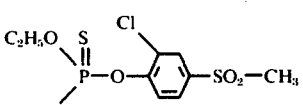 (5) | 0.1 0.02 | 100 90 |
| 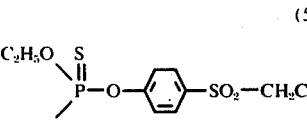 (2) | 0.1 0.02 | 100 70 |
| 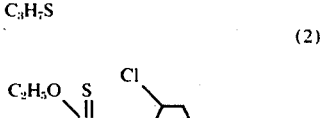 (3) | 0.1 0.02 | 100 55 |

The process of this invention is illustrated in the following preparative Examples.

EXAMPLE 7

The compound which were used as starting materials were prepared as follows:

(a)

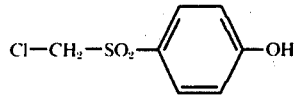 (IIb)

150 g (about 1.1 moles) of sulfuryl chloride were added dropwise, at 20° to 25° C, to a mixture of 140 g (1 mole) of 4-methylmercaptophenol, 880 g of ethylene chloride, 0.5 ml of concentrated sulfuric acid and 112 g (1.1 moles) of acetic anhydride. The mixture was acid was added until the mixture reacted strongly acid. After crystallization the product was filtered off and 167 g (81% of theory) of 4-chloromethylsulfonylphenol were obtained in the form of a colorless powder of melting point 110° C.

(b)

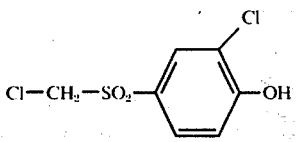 (IIc)

14.2 g (0.2 mole) of chlorine was passed into a solution of 41.5 g (0.2 mole) of 4-chloromethylsulphonylphenol in 200 ml acetic acid at 20° C. The mixture was stirred for a further 10 minutes and the solvent was then stripped off under reduced pressure. 100 ml of water were added to the residue and after crystallization the product was filtered off. 44.8 g (93% of theory) of 2-chloro-4-chloromethylsulfonylphenol were obtained in the form of a beige powder of melting point 108° C.

The following compounds were obtained analogously:

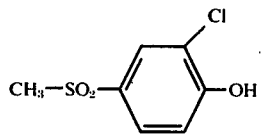
(IId)

Yield 84% of theory; melting point 161° C.

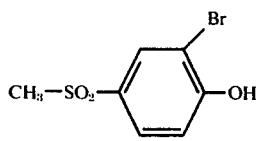
(IIe)

Yield 40% of theory; melting point 170° C.

(c)
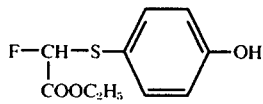
(IIf)

50.4 g (0.4 mole) of thiohydroquinone, followed by 56.2 g (0.4 mole) of fluorochloroacetic acid ethyl ester were added to a solution of 9.2 g (0.4 gram-atom) of sodium in 400 ml of ethanol at 20° to 25° C. The mixture was stirred for 3 days at 20° to 25° C and then poured into 1 liter of water.

After trituration, the product crystallized out and was filtered off. 49 g (53% of theory) of 4-(1'-fluoro-1'-car- bethoxy-methyl mercapto)-phenol were obtained in the form of colorless crystals of melting point 72° C.

EXAMPLE 8

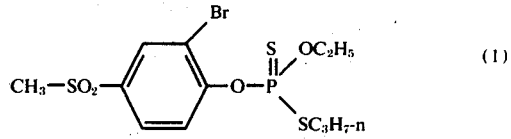

21.8 g (0.1 mole) of O-ethyl-S-n-propyl-thionothiolphosphoric acid diester chloride were added dropwise to a mixture of 25.1 g (0.1 mole) of 2-bromo-4-methylsulfonylphenol and 14.5 g (0.105 mole) of potassium carbonate in 200 ml of acetonitrile. The reaction was allowed to continue for 3 hours at 60° C; the salt-like precipitate was then filtered off and the filtrate was poured into 500 ml of toluene. The organic phase was washed with a sodium carbonate solution and with water and was dried over sodium sulfate. The solvent was then stripped off and the residue was purified by "slight distillation". 24 g (55% of theory) of O-ethyl-S-n-propyl-O-(2-bromo-4-methylsulfonylphenyl)-thionothiolphosphoric acid ester were obtained in the form of a yellow oil with a refractive index $n_D^{26}$ of 1.5806.

The following compounds were similarly synthesized:

| Compound No. | Formula | Refractive index | Yield (% of theory) |
|---|---|---|---|
| (2) | Cl—CH₂—SO₂—⟨phenyl⟩—O—P(=S)(OC₂H₅)(SC₃H₇-n) | $n_D^{24} = 1.5703$ | 82 |
| (3) | Cl—CH₂—SO₂—⟨phenyl-Cl⟩—O—P(=S)(OC₂H₅)(SC₃H₇-n) | $n_D^{25} = 1.5750$ | 57 |
| (4) | C₂H₅O—CO—CHF—S—⟨phenyl⟩—O—P(=S)(OC₂H₅)(SC₃H₇-n) | $n_D^{24} = 1.5552$ | 85 |
| (5) | CH₃—SO₂—⟨phenyl-Cl⟩—O—P(=S)(OC₂H₅)(SC₃H₇-n) | $n_D^{22} = 1.5695$ | 54 |
| (6) | CH₃—SO₂—⟨phenyl⟩—O—P(=S)(OC₂H₅)(SC₃H₇-n) | $n_D^{20} = 1.5592$ | 75 |

Other compounds which can be similarly prepared include:
O-tert.butyl-S-methyl-O-[2-fluoro-4-(4'-bromobutylsulfonyl)-phenyl]-thionothiolphosphoric acid ester,
O-isopropyl-S-ethyl-O-[4-(1', 3'-dichloroisopropylsulfonyl)-phenyl]-thionothiolphosphoric acid ester,
O-ethyl-S-n-propyl-O-[4-(1'-fluoro-carbomethoxymethylmercapto)-phenyl]-thionothiolphosphoric acid ester, and the like.

It will be appreciated that the instant specification and examples are set forth by way of illustration and not limitation, and that various modifications and changes may be made without departing from the spirit and scope of the present invention.

What is claimed is:

1. An O-phenylthionothiolphosphoric acid ester of the formula

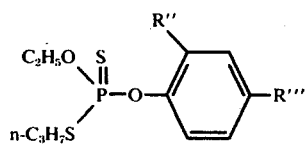

in which
R'' is hydrogen or halogen, and
R''' is lower alkylsulfonyl, halogeno-lower alkylsulfonyl or 1-fluoro-1-carbo-lower alkoxymethylmercapto.

2. A compound according to claim 1, in which R'' is hydrogen, chlorine or bromine, and R''' is alkylsulfonyl with 1 to 3 carbon atoms, chloromethylsulfonyl, 2-chloroethylsulfonyl, or 1-fluoro-carbalkoxymethylmercapto with 1 to 3 carbon atomms in the alkyl group.

3. The compound according to claim 1 wherein such compound is O-ethyl-S-n-propyl-O-(2-bromo-4-methylsulfonylphenyl)-thionothiolphosphoric acid ester of the formula

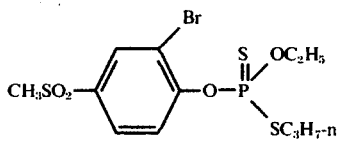

4. The compound according to claim 1 wherein such compound is O-ethyl-S-n-propyl-O-(4-chloromethylsulfonylphenyl)-thionothiolphosphoric acid ester of the formula

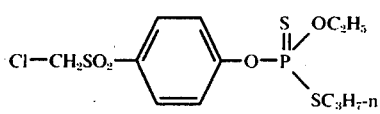

5. The compound according to claim 1 wherein such compound is O-ethyl-S-n-propyl-O-(2-chloro-4-chloromethylsulfonylphenyl)-thionothiolphosphoric acid ester of the formula

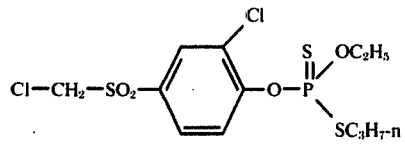

6. The compound according to claim 1 wherein such compound is O-ethyl-S-n-propyl-O-[4-(1'-fluoro-1'-carbethoxy-methylmercapto)-phenyl]-thionothiolphosphoric acid ester of the formula

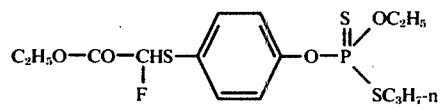

7. The compound according to claim 1 wherein such compound is O-ethyl-S-n-propyl-O-(2-chloro-4-methylsulfonylphenyl)-thionothiolphosphoric acid ester of the formula

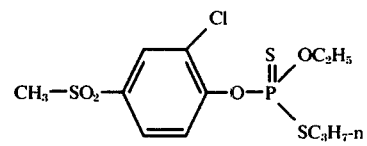

8. The compound according to claim 1 wherein such compound is O-ethyl-S-n-propyl-O-(4-methylsulfonylphenyl)-thionothiolphosphoric acid ester of the formula

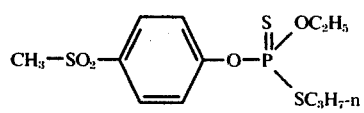

9. An insecticidal or acaricidal composition containing as active ingredient an insecticidally or acaricidally effective amount of a compound according to claim 1 in admixture with a diluent.

10. A method of combating insects or acarids which comprises applying to the insects or acarids, or to a habitat thereof, an insecticidally or acaricidally effective amount of a compound according to claim 1.

11. A method according to claim 9 in which said compound is
O-ethyl-S-n-propyl-O-(2-bromo-4-methylsulfonylphenyl)thionothiolphosphoric acid ester,
O-ethyl-S-n-propyl-O-(4-chloromethylsulfonylphenyl)thionothiolphosphoric acid ester,
O-ethyl-S-n-propyl-O-(2-chloro-4-chloromethylsulfonylphenyl)-thionothiolphosphoric acid ester,
O-ethyl-S-n-propyl-O-[4-(1'-fluoro-1'-carbethoxy-methylmercapto)-phenyl]-thionothiolphosphoric acid ester,
O-ethyl-S-n-propyl-O-(2-chloro-4-methylsulfonylphenyl)thionothiolphosphoric acid ester, or
O-ethyl-S-n-propyl-O-(4-methylsulfonylphenyl)-thionothiolphosphoric acid ester.

* * * * *